United States Patent
Wade et al.

[11] 3,940,397
[45] Feb. 24, 1976

[54] 2-[(SUBSTITUTED-PIPERAZINYL)ALKYL]-1H-BENZ[DE]ISOQUINOLINE-1,3(2H)-DIONES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Nov. 13, 1974

[21] Appl. No.: 523,293

[52] U.S. Cl............................ 260/268 TR; 424/250
[51] Int. Cl.²...................................... C07D 401/06
[58] Field of Search............... 260/268 TR; 424/250

Primary Examiner—Richard J. Gallagher
Assistant Examiner—Jose Tovar
Attorney, Agent, or Firm—Lawrence S. Levinson; Merle J. Smith; Stephen B. Davis

[57] ABSTRACT

Compounds of the following formula and their acid addition salts

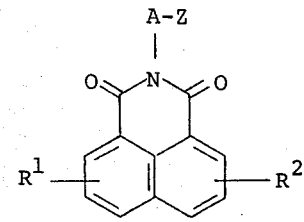

wherein $R^1$ and $R^2$ are independently selected from hydrogen, halogen, lower alkyl, lower alkoxy, lower alkylthio, nitro, cyano, amino and trifluoromethyl; A is a straight or branched chain alkylene of 1 to 8 carbons; and Z is

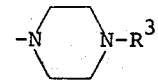

wherein $R^3$ is selected from phenyl, phenyl-lower alkyl, and substituted phenyl and phenyl-lower alkyl are disclosed. These compounds exhibit antidepressant activity. In addition these compounds are useful as anti-inflammatory agents.

22 Claims, No Drawings

2-[(SUBSTITUTED-PIPERAZINYL)ALKYL]-1H-BENZ[DE]ISOQUINOLINE-1,3(2H)-DIONES

BACKGROUND OF THE INVENTION

Various naphthalimide compounds have been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl]-1H-benz[de]isoquinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Carron et al. in French Pat. No. 2,167,355 disclose that (4-phenyl)piperidine-2,6-diones having an alkylheteroalkyl substituent at the 1-position possess antidepressant activity. Imides having a nitroimidazolyethyl group as an N-substituent and possessing anti-bacterial and anti-protozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al. Wu et al. in U.S. Pat. Nos. 3,398,151 and 3,558,777 and in the Journal of Med. Chem., Vol. 12, p. 876–881 (1969) disclose azaspirodecanediones having a (4-phenyl-1-piperazinyl)-alkylene group attached to the N atom which possess various pharmacological activities including muscle relaxant and antinflammatory activity. Mennear in U.S. Pat. No. 3,541,098 disclose 1,2-cyclobutanedicarboximides having a [4-(chlorophenyl)-1-piperazinyl]alkylene group attached to the N atom which possess central nervous system depressant activity and have useful analgesic and sedative properties.

SUMMARY OF THE INVENTION

This invention relates to new 2-[(substituted-piperazinyl)alkyl]-1H-benz[de]isoquinoline-1,3(2H)-diones and their acid addition salts of the formula

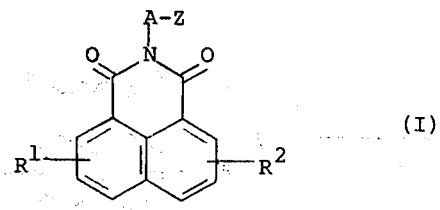

(I)

The symbols have the following meaning in formula I and throughout this specification.

$R^1$ and $R^2$ are each independently selected from hydrogen, halogen (preferably Br, Cl, or F), $CF_3$, lower alkyl, lower alkoxy, lower alkylthio, nitro, amino and cyano.

A is straight or branched chain alkylene of 1 to 8 carbons.

Z is

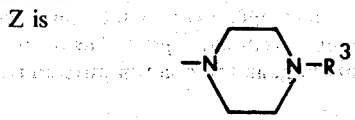

wherein $R^3$ is selected from phenyl, phenyl-lower alkyl, and substituted phenyl and phenyl-lower alkyl.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The phenyl-lower alkyl groups include such lower alkyl groups attached to a phenyl, e.g., benzyl, phenethyl, etc. The lower alkylthio group include such lower alkyl groups attached to a sulfur, e.g., methylthio, ethylthio, etc.

Straight or branched chain alkylene of 1 to 8 carbons is intended to include groups such as $-(CH_2)_n-$ wherein $n$ is 1 to 8,

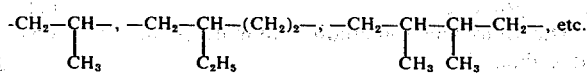

The substituted phenyl and phenyl-lower alkyl groups include one or more substituents such as lower alkyl, lower alkoxy, lower alkylthio, halogen (preferably F, Cl, or Br), $CF_3$, amino, nitro and the like. Examples of the type of groups contemplated are o-, m- or p-chlorophenyl, o-, m-, or p-tolyl, 2,5-dibromophenyl, 3,5-dimethylphenyl, o-, m-, or p-methoxyphenyl, o-, m-, or p-chlorobenzyl, o-, m-, or p-methoxybenzyl, o-, m-, or p-bromophenethyl, etc.

Preferred embodiments of this invention are as follows:

At least one of $R^1$ or $R^2$ is hydrogen and the other is hydrogen, Cl, F, Br, $CH_3$ or $OCH_3$.

A is straight or branched chain alkylene of 1 to 6 carbon atoms.

The most preferred compounds are:

$R^1$ and $R^2$ are both hydrogen.

A is $-(CH_2)_n-$ wherein $n$ is an integer from 2 to 6.

The new compounds of this invention are prepared by the following reactions where A is straight or branched chain alkylene of 2 to 8 carbons.

The substituted naphthalic anhydride of formula II

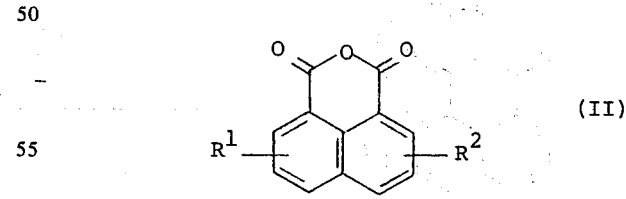

(II)

is reacted with an alkanolamine of formula III $H_2N-A-OH$  (III)

to yield the alcohol of formula IV

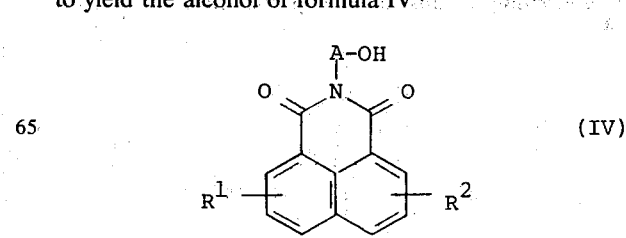

(IV)

The alcohol of formula IV is converted to the intermediate of formula V

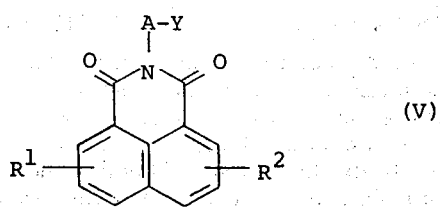

where Y is a leaving group such as tosylate, methanesulfonate or halogen by treating the alcohol with p-toluenesulfonyl chloride, methanesulfonyl chloride, thionyl chloride, thionyl bromide or hydrogen iodide.

The intermediate of formula V is then converted to the final products of formula I by reactions with compounds of the formula HZ.

The substituted naphthalic anhydride of formula II can be converted directly to the final products of formula I by reacting the anhydride with compounds of formula VI.

$$H_2N-A-Z \quad (VI)$$

The following schematic summarizes the reactions described above.

where A is straight or branched chain alkylene of 2 to 8 carbons

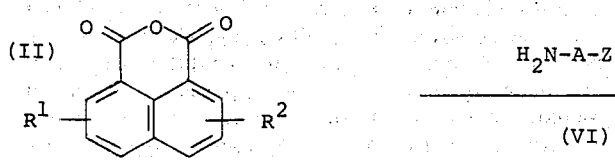
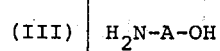
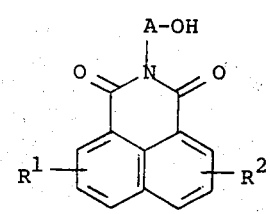

Also, the intermediate of formula V can be prepared by combining a substituted naphthalimide of formula VII

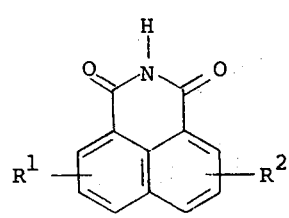

in an organic solvent with a polar organic solvent solution of a base, as for example an alcohol solution of potassium hydroxide, followed by the addition of a solution of the compound of formula VIII, $$Y'-A-Y \quad (VIII)$$

wherein Y' and Y are the same or different and are leaving groups selected from tosylate, methanesulfonate, or halogen and A is a straight or branched chain alkylene of 2 to 8 carbons.

Alternatively, the compounds of formula I wherein A is straight or branched alkylene of 2 to 8 carbons can be prepared by combining the anion of the substituted naphthalimide of formula VII, described above, with a solution of the compound of formula IX, $$Y-A-Z \quad (IX)$$

wherein Y is a leaving group as previously defined.

Compounds of formula I where A is —CH$_2$— are prepared by reacting the substituted naphthalimide of formula VII suspended in a polar organic solvent such as dimethylformamide (DMF) with compounds of the formula HZ and a source of formaldehyde such as aqueous formaldehyde or paraformaldehyde.

The various starting materials such as the substituted anhydrides of formula II and the alcohols of formula IV and the substituted naphthalimides of formula VII are known in the art or are readily obtainable by known

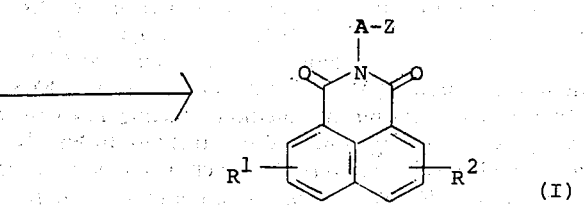
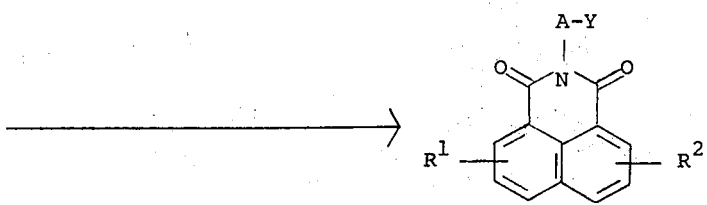

procedures. Further process details are also provided in the illustrative examples.

The compounds of formula I wherein either or both $R^1$ and $R^2$ are amine or $R^3$ is an amino substituted phenyl or phenyl-lower alkyl are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The new compounds of the present invention including the acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit antidepressant activity. A preferred dosage regimen for optimum results would be from about 1 mg. to about 5 mg. per kg. of body weight per day, and such dosage units are employed so that a total of from about 35 mg. to about 3 g. of active ingredient in single or divided doses are administered in a 24 hour period.

The antidepressant activity of the compounds of formula I is demonstrated by their ability to antagonize tetrabenazine-induced ptosis according to the procedure of Vernier et al. ("The Pharmacodynamics of Amitriptyline", *Psychosomatic Medicine*,](1962), pages 683–690) and also by their ability to block the reuptake of monoamines in vitro according to the procedure of Horn et al. (*Molecular Pharmacology*, 7th Ed., (1971), page 66).

The compounds of formula I are also useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg. to about 15 mg. per kg. of body weight per day.

For any of these pharmaceutical purposes a compound or mixture of compounds of formula I or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

2-[2-(4-Phenyl-1-piperazinyl)ethyl]-1H-benz[de]isoquinoline-1,3(2H)-dione, hydrochloride (1:2)

a. 2-(2-Hydroxyethyl)-1H-benz[de]isoquinoline-1,3(2H)-dione 50 g. (0.252 mole) of naphthalic anhydride and 16 g. (0.262 mole) of ethanolamine are refluxed for 3 hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b. 2-(2-Hydroxyethyl)-1H-benz[de]isoquinoline-1,3(2H)-dione, 4-methylbenzenesulfonate ester 52 g. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c. 2-[2-(4-Phenyl-1-piperazinyl)ethyl]-1H-benz[de]isoquinoline-1,3(2H)-dione, hydrochloride (1:2)

10 g. (0.025 mole) of the ester from part (b), 4.3 g. (0.026 mole) of N-phenylpiperazine, and 3.27 g. (0.025 mole) of diisopropylethylamine are refluxed in 500 ml. of toluene for 4 hours. The reaction mixture is then shaken with 5% NaOH, filtered, washed with water (all aqueous layers are backwashed with toluene), and shaken with 10% HCl. The precipitate that forms is filtered and washed with water and toluene. Recrystallization from water/ethanol yields 3.0 g. of 2-[2-(4-phenyl-1-piperazinyl)ethyl]-1H-benz[de]isoquinoline-1,3(2H)-dione, hydrochloride (1:2); m.p. 286°–287° (dec.).

EXAMPLE 2

2-[2-[4-(4-Methoxyphenyl)-1-piperazinyl]ethyl-1H-benz[de]isoquinoline-1,3(2H)-dione, hydrochloride (1:2)

Following the procedure of example 1 but substituting 5.1 g. (0.026 mole) of 1-(p-methoxyphenyl)piperazine for the N-phenylpiperazine in part (c), one obtains 8.0 g. of 2-[2-[4-(4-methoxyphenyl)-1-piperazinyl]etny]-1H-benz[de]-isoquinoline-1,3(2H)-dione, hydrochloride (1:2); m.p. 270°– 271° (dec.).

EXAMPLE 3

2-[2-[4-(2-Methoxyphenyl)-1-piperazinyl]etnyl]-1H-benz[de]-isoquinoline-1,3(2H)-dione, hydrochloride (1:2)

Following the procedure of example 1 but substituting 5.1 g. (0.026 mole) of 1-(o-methoxyphenyl)piperazine for the N-phenylpiperazine in part (c), one obtains 2.9 g. of 2-[47 2-[4-(2-methoxyphenyl)-1-piperazinyl]ethyl]-1H-benz[de]isoquinoline-1,3(2H)-dione, hydrochloride (1:2); m.p. 284° (dec.).

EXAMPLE 4

2-[2-[4-(4-Chlorophenyl)-1-piperazinyl]ethyl]-1H-benz[de]isoquinoline-1,3(2H)-dione, hydrochloride (1:1)

Following the procedure of example 1 but substituting 5.2 g. (0.026 mole) of 1-(p-chlorophenyl)piperazine in part (c) for the N-phenylpiperazine, one obtains 3.0 g. of 2-[2-[4-(4-chlorophenyl)-1-piperazinyl]e- thyl]-1H-benz[de]isoquinoline-1,3(2H)-dione, hydrochloride (1:1); m.p. 286°–287° (dec.).

EXAMPLE 5

2-[2-[4-(2-Chlorophenyl)-1-piperazinyl]ethyl]-1H-benz[de]-isoquinoline-1,3(2H)-dione Following the procedure of example 1 but substituting 5.2 g. (0.026 mole) of 1-(o-chlorophenyl)piperazine in part (c) for the N-phenylpiperazine, one obtains the hydrochloride salt of 2-[2-[4-(2-chlorophenyl)-1-piperazinyl]ethyl]-1H-benz[de]isoquinoline-1,3(2H)-dione. This salt is neutralized with aqueous sodium hydroxide and extracted with chloroform. The chloroform solution is dried ($Na_2SO_4$), concentrated to 200 ml. and allowed to stand open to the air. The product slowly crystallizes and is removed by filtration. Drying at 50° (60 mm.) overnight yields 4 g. of 2-[2-[4-(2-chlorophenyl)-1-piperazinyl]ethyl]-1H-benz-[de]isoquinoline-1,3(2H)-dione; m.p. 213°–214°.

EXAMPLE 6

2-[2-[4-[3-(Trifluoromethyl)phenyl]-1-piperazinyl]ethyl]-1H-benz[de]isoquinoline-1,3(2H)-dione, hydrochloride (1:1)

Following the procedure of example 1 but substituting 6.1 g. (0.026 mole) of 1-[3-(trifluoromethyl)phenyl]piperazine for the N-phenylpiperazine in part (c), one obtains 6.53 g. of 2-[2-[4-[3-(trifluoromethyl)phenyl]-1-piperazinyl]ethyl]-1H-benz-[de]isoquinoline-1,3(2H)-dione, hydrochloride (1:1); m.p. 276°–277° (dec.).

EXAMPLE 7

2-[2-[4-(4-Fluorophenyl)-1-piperazinyl]ethyl]-1H-benz[de]isoquinoline-1,3(2H)-dione, hydrochloride (1:1)

Following the procedure of example 1 but substituting 4.8 g. (0.026 mole) of 1-(p-fluorophenyl)piperazine for the N-phenylpiperazine in part (c), one obtains 6.1 g. of 2-[2-[4-(4-fluorophenyl)-1-piperazinyl]ethyl]-1H-benz[de]isoquinoline-1,3(2H)-dione, hydrochloride (1:1); m.p. 309°–310° (dec.).

EXAMPLE 8

2-[2-[4-(Phenylmethyl)-1-piperazinyl]ethyl]-1H-benz-[de]isoquinoline-1,3(2H)-dione, hydrochloride (1:2)

Following the procedure of example 1 but substituting 4.7 g. (0.026 mole) of 1-(phenylmethyl)piperazine for the N-phenylpiperazine in part (c), one obtains 10.8 g. of 2-[2-[4-(phenylmethyl)-1-piperazinyl]ethyl]-1H-benz[de]isoquinoline-1,3(2H)-dione, hydrochloride (1:2); preliminary melting at 278°–281° and final melting with decomposition at 284°.

EXAMPLES 9–22

Following the procedure of example 1 but substituting for the N-phenylpiperazine in part (c) an equivalent amount of one of the following:

1-(2-phenylethyl)piperazine
1-(3-phenylpropyl)piperazine
1-(4-phenylbutyl)piperazine
1-(3,5-dichlorophenyl)piperazine
1-(4-ethylphenyl)piperazine
1-(4-nitrophenyl)piperazine
1-(2-thiopropylphenyl)piperazine
1-(3-trifluoromethyl-4-chlorophenyl)piperazine
1-(3-trifluoromethyl-4-methylphenyl)piperazine
1-[(4-bromophenyl)methyl]piperazine
1-[2-(4-chlorophenyl)ethyl]piperazine
1-[[(3-trifluoromethyl)phenyl]methyl]piperazine
1-[3-(4-methylphenyl)propyl]piperazine
1-[(3,5-dimethoxyphenyl)methyl]piperazine one obtains 2-[2-[4-(2-phenylethyl)-1-piperazinyl]ethyl]-1H-benz[de]-isoquinoline-1,3(2H)-dione, hydrochloride;
2-[2-[4-(3-phenylpropyl)-1-piperazinyl]ethyl]-1H-benz[de]-isoquinoline-1,3(2H)-dione, hydrochloride;
2-[2-[4-(4-phenylbutyl)-1-piperazinyl]ethyl]-1H-benz[de]-isoquinoline-1,3(2H)-dione, hydrochloride;
2-[2-[4-(3,5-dichlorophenyl)-1-piperazinyl]ethyl]-1H-benz[de]isoquinoline-1,3(2H)-dione, hydrochloride;
2-[2-[4-(4-ethylphenyl)-1-piperazinyl]ethyl]-1H-benz[de]-isoquinoline-1,3(2H)-dione, hydrochloride;
2-[2-[4-(4-nitrophenyl)-1-piperazinyl]ethyl]-1H-benz[de]isoquinoline-1,3(2H)-dione, hydrochloride;
2-[2-[4-(2-thiopropylphenyl)-1-piperazinyl]ethyl]-1H-benz[de]isoquinoline-1,3(2H)-dione, hydrochloride;
2-[2-[4-(3-trifluoromethyl-4-chlorophenyl)-1-piperazinyl]ethyl]-1H-benz[de]isoquinoline-1,3(2H)-dione, hydrochloride;
2-[2-[4-(3-trifluoromethyl-4-methylphenyl)-1-piperazinyl]ethyl]-1H-benz[de]isoquinoline-1,3(2H)-dione, hydrochloride;
2-[2-[4-[(4-bromophenyl)methyl]-1-piperazinyl]ethyl]-1H-benz[de]isoquinoline-1,3(2H)-dione, hydrochloride;
2-[2-[4-[2-(4-chlorophenyl)ethyl]-1-piperazinyl]ethyl]-1H-benz[de]isoquinoline-1,3(2H)-dione, hydrochloride;
2-[2-[4-[[(3-trifluoromethyl)phenyl]methyl]-1-piperazinyl]-ethyl]-1H-benz[de]isoquinoline-1,3(2H)-dione, hydrochloride;
2-[2-[4-[3-(4-methylphenyl)propyl]-1-piperazinyl]ethyl]-1H-benz[de]isoquinoline-1,3(2H)-dione, hydrochloride; and
2-[2-[4-[(3,5-dimethoxyphenyl)methyl]-1-piperazinyl]ethyl]-1H-benz[de]isoquinoline-1,3(2H)-dione, hydrochloride; respectively.

EXAMPLE 23

2-[3-(4-Phenyl-1-piperazinyl)propyl]-1H-benz-[de]isoquinoline-1,3(2H)-dione, hydrochloride a. 2-(3-Hydroxypropyl)-1H-benz[de]isoquinoline-1,3(2H)-dione, 4-methylbenzenesulfonate ester Following the procedure of example 1(a) and (b) but substituting 3-aminopropanol for the ethanolamine in part (a) one obtains 2-(3-hydroxypropyl)-1H-benz[de]isoquinoline-1,3(2H)-dione, 4-methylbenzenesulfonate ester.

b. 2-[3-(4-Phenyl-1-piperazinyl)propyl]-1H-benz[de]isoquinoline-1,3(2H)-dione, hydrochloride Following the procedure of example 1(c) but substituting an equivalent amount of 2-(3-hydroxypropyl)-1H-benz[de]isoquinoline-1,3(2H)-dione, 4-methylbenzenesulfonate ester for the ester in example 1(c), one obtains 2-[3-(4-phenyl-1-piperazinyl)propyl]-1H-benz[de]isoquiniline-1,3(2H)-dione, hydrochloride.

EXAMPLE 24

2-[4-(4-Phenyl-1-piperazinyl)butyl]-1H-benz[de]isoquinoline-1,3-(2H)-dione, hydrochloride a. 2-(4-Hydroxybutyl)-1H-benz[de]isoquinoline-1,3(2H)-dione, 4-methylbenzenesulfonate ester Following the procedure of example 1(a) and (b) but substituting 4-aminobutanol for the ethanolamine in part (a) one obtains 2-(4-hydroxybutyl)-1H-benz[de]isoquinoline-1,3(2H)-dione, 4-methylbenzenesulfonate ester.

b. 2-[4-(4-Phenyl-1-piperazinyl)butyl]-1H-benz[de]isoquinoline-1,3-(2H)-dione, hydrochloride Following the procedure of example 1(c) but substituting an equivalent amount of 2-(4-hydroxybutyl)-1H-benz[de]isoquinoline-1,3(2H)-dione, 4-methylbenzenesulfonate ester for the ester in example 1(c), one obtains 2-[4-(4-phenyl-1-piperazinyl)butyl]-1H-benz[de]isoquinoline-1,3(2H)-dione, hydrochloride.

EXAMPLES 25–33

Following the procedure of example 1 but substituting the alkanolamine shown in Col. I for the ethanolamine the following products are obtained wherein A is the radical shown in Col. II.

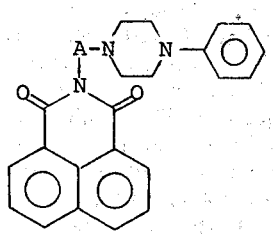

| Ex. | Col. I | Col. II |
|---|---|---|
| 25 | $H_2N-(CH_2)_5-OH$ | $-(CH_2)_5-$ |
| 26 | $H_2N-(CH_2)_6-OH$ | $-(CH_2)_6-$ |
| 27 | $H_2N-(CH_2)_7-OH$ | $-(CH_2)_7-$ |
| 28 | $H_2N-(CH_2)_8-OH$ | $-(CH_2)_8-$ |
| 29 | $H_2N-CH_2-\underset{CH_3}{CH}-CH_2-OH$ | $-CH_2-\underset{CH_3}{CH}-CH_2-$ |
| 30 | $H_2N-\underset{CH_3}{CH}-(CH_2)_3-OH$ | $-\underset{CH_3}{CH}-(CH_2)_3-$ |
| 31 | $H_2N-(CH_2)_3-\underset{CH_3}{CH}-OH$ | $-(CH_2)_3-\underset{CH_3}{CH}-$ |
| 32 | $H_2N-CH_2-\underset{C_3H_7}{CH}-(CH_2)_2-OH$ | $-CH_2-\underset{C_3H_7}{CH}-(CH_2)_2-$ |
| 33 | $H_2N-\underset{CH_3}{CH}-CH_2-\underset{CH_3}{CH}-OH$ | $-\underset{CH_3}{CH}-CH_2-\underset{CH_3}{CH}-$ |

Similarly, by employing the substituted piperazines of examples 2 to 22 in the procedures of examples of 23 to 33, other compounds within the scope of this invention are prepared.

EXAMPLE 34

2-[4-(4-Phenyl-1-piperazinyl)butyl]-1H-benz[de]isoquinoline-1,3(2H)-dione, hydrochloride (1:1)

a. 2-(4-Bromobutyl)-1H-benz[de]isoquinoline-1,3(2H)-dione 100 g. (0.5 mole) of 1,8-naphthalimide is suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for 1 hour at 90° and cooled to 25°. 245 g. (1.0 mole) of 1,4-dibromobutane is added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(4-bromobutyl)-1H-benz[de]isoquinoline-1,3(2H)-dione. The precipitate is filtered off, washed with fresh hexane and dried for 2hours at 50° (0.1 mm.) to yield 2-(4-bromobutyl)-1H-benz[de]isoquinoline-1,3(2H)-dione. An analytically pure sample is prepared by dissolving the above product in hot 95% ethanol and recrystallizing by allowing the solution to cool to 25°. The resulting precipitate is dried for 2 hours at 50° (0.1 mm.) to yield pure 2-(4-bromobutyl)-1H-benz[de]isoquinoline-1,3(2H)-dione, m.p. 113°–115°.

b. 2-[4-(4-Phenyl-1-piperazinyl)butyl]-1H-benz[de]isoquinoline-1,3(2H)-dione, hydrochloride (1:1)

9.0 g. (0.027 mole) of 2-(4-bromobutyl)-1H-benz[de]isoquinoline-1,3(2H)-dione from part (a) and 4.5 g. (0.027 mole) of N-phenylpiperazine are refluxed for 2 days over excess anhydrous sodium carbonate. The reaction mixture is washed with water and backwashed with toluene. The combined organic layers are washed with water twice and shaken with 10% HCl for one hour. The resulting precipitate is filtered from the two phases, washed with water and toluene, and dried in vacuo at 100° for 1 hour to yield 9.33 g. of 2-[4-(4-phenyl-1-piperazinyl)butyl]-1H-benz[de]isoquinoline-1,3(2H)-dione, hydrochloride (1:1); m.p. 265°–267° (dec.).

EXAMPLE 35

2-[6-(4-Phenyl-1-piperazinyl)hexyl]-1H-benz[de]isoquinoline-1,3-(2H)-dione, hydrochloride a. 2-(6-Bromohexyl)-1H-benz[de]isoquinoline-1,3(2H)-dione Following the procedure of part (a) of example 34 but substituting 1,6-dibromohexane for 1,4-dibromobutane, one obtains 2-(6-bromohexyl)-1H-benz[de]isoquinoline-1,3(2H)-dione; m.p. 95°–96°.

b. 2-[6-(4-Phenyl-1-piperazinyl)hexyl]-1H-benz[de]isoquinoline-1,3(2H)-dione, hydrochloride Following the procedure of part (b) of example 34 but substituting 2-(6-bromohexyl)-1H-benz[de]isoquinoline-1,3(2H)-dione for the 2-(4-bromobutyl)-1H-benz[de]isoquinoline-1,3-(2H)-dione, one obtains 2-[6-(4-phenyl-1-piperazinyl)hexyl]-1H-benz[de]isoquinoline-1,3(2H)-dione, )-dione, hydrochloride.

EXAMPLE 36

2-[5-(4-Phenyl-1-piperazinyl)pentyl]-1H-benz[de]isoquiniline-1,3(2H)-dione, hydrochloride a. 2-(5-Bromopentyl)-1H-benz[de]isoquinoline-1,3(2H)-dione Following the procedure of part (a) of example 34 but substituting 1,5-dibromopentane for the 1,4- dibromobutane, one obtains 2-(5-bromopentyl)-1H-benz[de]isoquinoline-1,3(2H)-dione; m.p. 113°–115°.

b. 2-[5-(4-Phenyl-1-piperazinyl)pentyl]-1H-benz[de]isoquinoline-1,3(2H)-dione, hydrochloride Following the procedure of part (b) of example 34 but substituting 2-(5-bromopentyl)-1H-benz[de]isoquinoline-1,3(2H)-dione for the 2-(4-bromobutyl)-1H-benz[de]isoquinoline-1,3(2H)-dione, one obtains 2-[5-(4-phenyl-1-piperazinyl)pentyl]-1H-benz[de]isoquinoline-1,3(2H)-dione, hydrochloride.

Alternatively, the procedure of examples 34–36.can be employed to prepare the compounds of examples 1–33.

EXAMPLE 37

2-[(4-Phenyl-1-piperazinyl)methyl]-1H-benz[de]isoquinoline-1,3,-(2H)-dione

An equimolar mixture of N-phenylpiperazine, aqueous formaldehyde, and 1,8-naphthalimide is suspended in a small amount of dimethylformamide and the mixture is heated until dissolution is complete. The solution is allowed to stand at room temperature and the resulting precipitate is filtered off and dried to yield 2-[(4-phenyl-1-piperazinyl)methyl]-1H-benz[de]isoquinoline-1,3(2H)-dione.

Similarly, by employing the various substituted piperazines of Examples 2 to 22 in the above procedure, other compounds within the scope of the invention are prepared.

EXAMPLE 38

5-Chloro-2-[2-(4-phenyl-1-piperazinyl)ethyl]-1H-benz[de]isoquinoline-1,3(2H)-dione, hydrochloride (1:1)

a. 5-Chloro-2-(2-hydroxyethyl)-1H-benz[de]isoquinoline-1,3(2H)-dione, 4-methylbenzenesulfonate ester Following the procedure of Example 1(a) and (b) but substituting 3-chloronaphthalic anhydride for the naphthalic anhydride one obtains 5-chloro-2-(2-hydroxyethyl)-1H-benz[de]isoquinoline-1,3(2H)-dione, 4-methylbenzenesulfonate ester.

b. 5-Chloro-2-[2-(4-phenyl-1-piperazinyl)ethyl]-1H-benz[de]-isoquinoline-1,3(2H)-dione, hydrochloride (1:1)

10 g. (0.023 mole) of the ester from part (a) and 7.6 g. (0.049 mole) of N-phenylpiperazine are refluxed in 300 ml. of toluene for 1 hour. The mixture is then cooled to 25° and after 3 hours the resulting precipitate is removed by filtration. The filtrate is shaken with excess 10% HCl (aqueous) producing a gum that is insoluble in both layers. After several minutes the gum crystallizes and is filtered from the two liquid phases. This crude material is digested for two hours at reflux temperature in 1000 ml. of 50% aqueous ethanol, cooled to 25°, filtered, and dried at 90° (0.1 mm.) for 4 hours to yield 5.2 g. of 5-chloro-2-[2-(4-phenyl-1-piperazinyl)ethyl]-1H-benz[de]isoquinoline-1,3(2H)-dione, hydrochloride (1:1); preliminary darkening at 284° followed by melting with decomposition at 286°–290°.

EXAMPLE 39

6-Chloro-2-[2-(4-phenyl-1-piperazinyl)etnlyl]-1H-benz[de]isoquinoline-1,3(2H)-dione, hydrochloride (1:1)

a. 6-Chloro-2-(2-chloroethyl)-1H-benz[de]isoquinoline-1,3(2H)-dione 25 g. (0.108 mole) of 4-chloronaphthalimide is dissolved in 300 ml. of warm dimethylformamide (ca. 80°). 7.1 g. (0.108 mole) of potassium hydroxide (85%) in 100 ml. of ethanol is added resulting in the formation of a precipitate. The resulting mixture is heated at about 90° for 30 minutes and 45 g. (0.32 mole) of 1-bromo-2-chloroethane in 100 ml. of dimethylformamide is added. After stirring for 1 hour, the mixture is cooled, poured into 3 liters of water and extracted with CHCl₃. The solution is evaporated to dryness and washed through a short (100 g.) column of alumina (Act. I) with CHCl₃. The solvent is removed under vacuum and the residue is digested for 30 minutes in boiling ethanol. The mixture is cooled to 25° and the precipitate is filtered off and dried to yield 13.6 g. of 6-chloro-2-(2-chloroethyl)-1H-benz[de]isoquinoline-1,3(2H)-dione.

b. 6-Chloro-2-[2-(4-phenyl-1-piperazinyl)ethyl]-1H-benz[de]isoquinoline-1,3(2H)-dione, hydrochloride (1:1)

5 g. (0.017 mole) of 6-chloro-2-(2-chloroethyl)-1H-benz[de]isoquinoline-1,3(2H)-dione, from part (a), 6g. (0.037 mole) of N-phenylpiperazine, and 2.2 g. (0.017 mole) of diisopropylethylamine are refluxed in 250 ml. of toluene for 48 hours. After cooling to 25°, the mixture is shaken with excess 10% HCl producing a precipitate that is insoluble in both liquid phases. The precipitated crude product is filtered off and purified by converting it back to free base (partition between 10% KOH and CHCl₃ and evaporating off the CHCl₃) and then washing it through a short column of alumina (50 × 170 mm. Act. I) with CHCl₃. The solvent is removed to give 3 g. of free base. This is again taken up in toluene and converted to the salt by shaking with 10% HCl (aqueous). The resulting precipitate is filtered from the two liquid phases, recrystallized from 66% aqueous ethanol, and dried for 12 hours at 70° (0.1 mm.) to yield 2.0 g. of 6-chloro-2-[2-(4-phenyl-1-piperazinyl)ethyl]-1H-benz[de]isoquinoline-1,3(2H)-dione, hydrochloride (1:1).

The melting point of the salt is indistinct. On rapid heating (10°–20°/minute), from 200°–265° the material changes color from yellow to gray to black. On slower heating from 265°–272° the black material collapses and at 272°–274° becomes fluid.

EXAMPLES 40-65

Following the procedure of example 1 but substituting for the 2-(2-hydroxyethyl)-1H-benz[de]isoquinoline-1,3(2H)-dione, 4-methylbenzenesulfonate ester the ester shown in Col. I one obtains the product shown in Col. II.

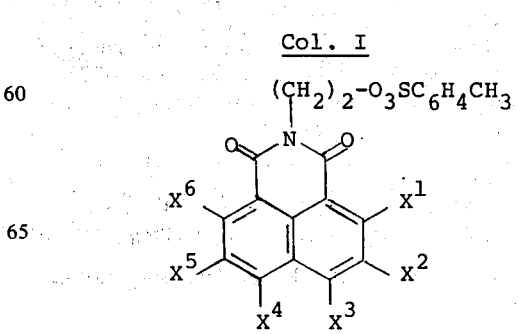

Col. I

Col. II

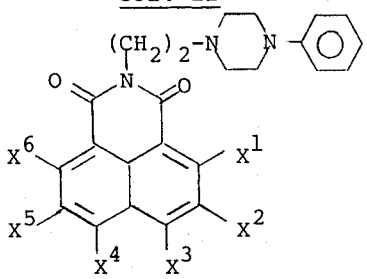

| Ex. | X¹ | X² | X³ | X⁴ | X⁵ | X⁶ |
|---|---|---|---|---|---|---|
| 40 | H | H | Br | H | H | H |
| 41 | H | Cl | H | H | H | H |
| 42 | H | Br | H | H | H | H |
| 43 | H | F | H | H | H | H |
| 44 | H | I | H | H | H | H |
| 45 | H | Cl | H | H | Cl | H |
| 46 | Br | H | H | H | H | H |
| 47 | H | H | Cl | Cl | H | H |
| 48 | H | H | CH₃ | H | H | H |
| 49 | H | H | C₂H₅ | H | H | H |
| 50 | H | H | i-C₃H₇ | H | H | H |
| 51 | H | H | CH₃ | CH₃ | H | H |
| 52 | H | H | OCH₃ | H | H | H |
| 53 | H | H | OC₂H₅ | H | H | H |
| 54 | H | H | OC₃H₇ | H | H | H |
| 55 | H | H | OCH₃ | OCH₃ | H | H |
| 56 | H | NO₂ | H | H | H | H |
| 57 | H | H | NO₂ | H | H | H |
| 58 | H | CF₃ | H | H | H | H |
| 59 | H | H | CF₃ | H | H | H |
| 60 | H | CN | H | H | H | H |
| 61 | H | H | CN | H | H | H |
| 62 | H | H | NH₂ | H | H | H |
| 63 | H | NH₂ | H | H | H | H |
| 64 | H | SC₃H₇ | H | H | H | H |
| 65 | H | H | SCH₃ | H | H | H |

Similarly, by employing the ester of Col. I of Examples 40–65 in the procedures of examples 2 to 33, other compounds within the scope of this invention are prepared. Similarly, by following the procedures of Example 34 but employing a substituted 1,8-naphthalimide of formula VII wherein the substituents are those listed under headings X¹, X², X³, X⁴, X⁵, and X⁶ in examples 40 to 65, other compounds within the scope of this invention are prepared.

What is claimed is:

1. A compound of the formula

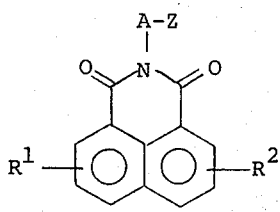

wherein R¹ and R² are each independently selected from the group consisting of hydrogen, halogen, lower alkyl, lower alkoxy, lower alkylthio, nitro, cyano, amino, and trifluoromethyl; A is a straight or branched chain alkylene of 1 to 8 carbons; and Z is

wherein R³ is selected from the group consisting of phenyl, phenyl-lower alkyl and substituted phenyl and phenyl-lower alkyl and said phenyl substituents are one or more selected from the group consisting of halogen, lower alkyl, lower alkoxy, lower alkylthio, nitro, amino, and trifluoromethyl; or the pharmaceutically acceptable acid addition salts thereof.

2. The compound of claim 1 wherein at least one of R¹ and R² is hydrogen and the other is selected from the group consisting of hydrogen, Cl, Br, F, methyl and methoxy; and A is a straight or branched chain alkylene of 1 to 6 carbons.

3. The compound of claim 2 having the name 2-[(4-phenyl-1-piperazinyl)methyl]-1H-benz[de]isoquinoline-1,3(2H)-dione.

4. The compound of claim 2 having the name 5-chloro-2-[2-(4-phenyl-1-piperazinyl)ethyl]-1H-benz[de]isoquinoline-1,3-(2H)-dione, hydrochloride (1:1).

5. The compound of claim 2 having the name 6-chloro-2-[2-(4-phenyl-1-piperazinyl)ethyl]-1H-benz[de]isoquinoline-1,3-(2H)-dione, hydrochloride (1:1).

6. The compound of claim 2 wherein R¹ and R² are both hydrogen and A is a straight chain alkylene of 2 to 6 carbons.

7. The compound of claim 6 wherein A is —(CH₂)₃—.

8. The compound of claim 6 wherein A is —(CH₂)₅—.

9. The compound of claim 6 wherein A is —(CH₂)₆—.

10. The compound of claim 6 wherein A is —(CH₂)₂—.

11. The compound of claim 10 having the name 2-[2-(4-phenyl-1-piperazinyl)ethyl]-1H-benz[de]isoquinoline-1,3(2H)-dione, hydrochloride (1:2).

12. The compound of claim 10 having the name 2-[2-[4-(4-methoxyphenyl)-1-piperazinyl]ethyl]-1H-benz[de]isoquinoline-1,3-(2H)-dione, hydrochloride (1:2).

13. The compound of claim 10 having the name 2-[2-[4-(2-methoxyphenyl)-1-piperazinyl]ethyl]-1H-benz[de]isoquinoline-1,3(2H)-dione, hydrochloride (1:2).

14. The compound of claim 10 having the name 2-[2-[4-(4-chlorophenyl)-1-piperazinyl]ethyl]-1H-benz[de]isoquinoline-1,3-(2H)-dione, hydrochloride (1:1).

15. The compound of claim 10 having the name 2-[2-[4-(2-chlorophenyl)-1-piperazinyl]ethyl]-1H-benz[de]isoquinoline-1,3(2H)-dione, hydrochloride (1:1).

16. The compound of claim 10 having the same 2-[2-[4-[3-(trifluoromethyl)phenyl]-1-piperazinyl]ethyl]-1H-benz[de]isoquinoline-1,3(2H)-dione, hydrochloride (1:1).

17. The compound of claim 10 having the name 2-[2-[4-(4-fluorophenyl)-1-piperazinyl]ethyl]-1H-benz[de]isoquinoline-1,3(2H)-dione, hydrochloride (1:1).

18. The compound of claim 10 having the name 2-[2-[4-(phenylmethyl)-1-piperazinyl]ethyl]-1H-benz[de]isoquinoline-1,3(2H)-dione, hydrochloride (1:1).

19. The compound of claim 6 wherein A is —(CH₂)₄—.

20. A compound of claim 19 having the name of 2-[4-(4-phenyl-1-piperazinyl)butyl]-1H-benz[de]isoquinoline-1,3(2H)-dione, hydrochloride (1:1).

21. A composition consisting essentially of a compound or mixture of compounds of claim 1 and a pharmaceutically acceptable carrier.

22. The method of treating depression comprising administering an effective amount of the composition of claim 21.

* * * * *

UNITED STATES PATENT AND TRADEMARK OFFICE
CERTIFICATE OF CORRECTION

PATENT NO. : 3,940,397
DATED : Feb. 24, 1976
INVENTOR(S) : Peter C. Wade et al.

It is certified that error appears in the above-identified patent and that said Letters Patent are hereby corrected as shown below:

Col. 6, line 45, "ny" at the beginning of the line should read --hyl--.

Col. 6, line 50, "etnyl" should read --ethyl--.

Col. 9, line 3, "isoquiniline" should read --isoquinoline--.

Col. 10, line 64, "isoquiniline" should read --isoquinoline--.

Signed and Sealed this twenty-second Day of June 1976

[SEAL]

Attest:

RUTH C. MASON
Attesting Officer

C. MARSHALL DANN
Commissioner of Patents and Trademarks